US009688557B2

United States Patent
Blank et al.

(10) Patent No.: US 9,688,557 B2
(45) Date of Patent: Jun. 27, 2017

(54) PROCESS OF TREATING BUCHU MERCAPTAN PRODUCTION WASTEWATER USING MICROALGAE AND CHITIN AS A NITROGEN SOURCE

(71) Applicant: The University of Montana, Missoula, MT (US)

(72) Inventors: Carrine Blank, Missoula, MT (US); Nancy W. Hinman, Missoula, MT (US)

(73) Assignee: The University of Montana, Missoula, MT (US)

( * ) Notice: Subject to any disclaimer, the term of this patent is extended or adjusted under 35 U.S.C. 154(b) by 0 days.

(21) Appl. No.: 14/818,011

(22) Filed: Aug. 4, 2015

(65) Prior Publication Data
US 2015/0329397 A1     Nov. 19, 2015

Related U.S. Application Data

(60) Continuation-in-part of application No. 14/181,387, filed on Feb. 14, 2014, now Pat. No. 9,102,552, which is a division of application No. 13/430,486, filed on Mar. 26, 2012, now Pat. No. 8,673,619.

(60) Provisional application No. 61/467,869, filed on Mar. 25, 2011.

(51) Int. Cl.
| | |
|---|---|
| *C12F 3/00* | (2006.01) |
| *C02F 3/32* | (2006.01) |
| *A01G 33/00* | (2006.01) |
| *C02F 3/34* | (2006.01) |
| *C12N 1/12* | (2006.01) |

(52) U.S. Cl.
CPC .............. *C02F 3/322* (2013.01); *A01G 33/00* (2013.01); *C02F 3/34* (2013.01); *C12N 1/12* (2013.01); *C02F 2101/40* (2013.01); *C02F 2303/02* (2013.01); *C02F 2305/06* (2013.01); *Y02W 10/37* (2015.05)

(58) Field of Classification Search
CPC ..... C02F 3/32; C02F 3/34; C12N 1/12; C12F 3/00
See application file for complete search history.

(56) References Cited

U.S. PATENT DOCUMENTS

| 6,579,714 B1 | 6/2003 | Hirabayashi et al. |
| 8,101,080 B2 | 1/2012 | Robinson et al. |

OTHER PUBLICATIONS

Donderski et al. The Utilization of N=Acetylglucosamine and Chitin as Sources of Carbond and Nitrongen by Planktonic and Benthic Bacteria in Lake Jeziorak; Polish Journal of Environmental Studies, vol. 12, No. 6 (2003) pp. 685-692.

Pouliced, M. et al., Chitin Biodegradation in Marine Environments; An Experimental Approach, Biochemical Systematics and Ecology, 1991, pp. 385-394, vol. 19, Pergamon Press, Great Britain.

Souza, C. et al., The Importance of Chitin in the Marine Environment, Mar Biotechnol. 2011, pp. 823-830, vol. 13, Springer Science+Business Media, LLC.

*Primary Examiner* — Scott Long
*Assistant Examiner* — Paul Martin
(74) *Attorney, Agent, or Firm* — Jean Kyle

(57) ABSTRACT

A process of growing a culture of cyanobacteria or algae using chitin or chitosan as a source of nitrogen for photosynthetic growth is described. This process can be used to remove pollutants from nitrogen-deficient natural waters or wastewaters including buchu mercaptan production wastewater. Biomass that results from photosynthetic growth on chitin can be used, either as whole cells or the isolated components of the cells, for a large variety of commercial purposes.

4 Claims, 4 Drawing Sheets

FIG. 1A

| Environment of Origin | Growth conditions | Type of Organism | Morphological Taxonomic Assignment | Molecular Assignment | Taxonomic |
|---|---|---|---|---|---|
| Commercial evaporated sea salt | Marine | Chlorophyta | *Dunaliella* | n.d. | |
| Commercial evaporated sea salt | Marine | Chlorophyta | *Chlorella* | n.d. | |
| Commercial evaporated sea salt | Marine | Cyanobacteria | *Leptolyngbya* | 96% identical to *Leptolyngbya* sp. LEGE 07312, SEQ ID NO: 1. | |
| Commercial evaporated sea salt | Marine | Cyanobacteria | *Nodularia* | 99% identical to *Nodularia harveyana*, SEQ ID NO: 2. | |
| Puget Sound water, Port Townsend, WA | Marine hypersaline | Eustigmatophyta | *Nannochloropsis* | 100% identical to *Nannochloropsis salina* chloroplast, SEQ ID NO: 3. | |

FIG. 1B

| Environment of Origin | Growth conditions | Type of Organism | Morphological Taxonomic Assignment | Molecular Taxonomic Assignment |
|---|---|---|---|---|
| Bitterroot River water, Missoula, MT | Freshwater | Chlorophyta | *Auxenochlorella* * | 98% identical to *Auxenochlorella prototheocoides* chloroplast, SEQ ID NO: 4. |
| Bitterroot River water, Missoula, MT | Freshwater | Diatom | *Cymbella* * | 97% identical to *Cymbella pisciculus* chloroplast, SEQ ID NO: 5. |
| Bitterroot River water, Missoula, MT | Freshwater | Cyanobacteria | *Synechococcus* * | 98% identical to *Synechococcus* PCC 7001, SEQ ID NO: 6. |
| Iron rich soil, Sedona, AZ | Freshwater | Diatom | *Cymbella* * | 99% identical to *Cymbella hauckii* chloroplast, SEQ ID NO: 7 |
| Iron rich soil, Sedona, AZ | Freshwater | Cyanobacteria | Novel cyanobacterium * | 95% identical to *Acaryochloris* sp. JJ7-5, SEQ ID NO: 8. |
| Iron rich soil, Sedona, AZ | Freshwater | Cyanobacteria | Unknown * | n.d. |
| Iron rich soil, Sedona, AZ | Freshwater | Cyanobacteria | *Leptolyngbya* | n.d. |

FIG. 1C

| Environment of Origin | Growth conditions | Type of Organism | Morphological Taxonomic Assignment | Molecular Taxonomic Assignment |
|---|---|---|---|---|
| Holland Lake Freshwater water, MT | | Cyanobacteria | *Cyanobium* | n.d. |
| Holland Lake Freshwater water, MT | | Cyanobacteria | *Synechococcus* | n.d. |
| Red Alkali Lake, WA | Alkaline, brackish | Chlorophyta | *Chlorella* | |
| Red Alkali Lake, WA | Alkaline, brackish | Cyanobacterium | *Cyanobium* | 93% identical to *Synechococcus* RCC1026, SEQ ID NO: 9. |
| Red Alkali Lake, WA | Alkaline, brackish | Cyanobacterium | *Nostoc* | n.d. |
| Soap Lake, WA | Alkaline, brackish | Cyanobacterium | *Cyanobium* | 98% identical to *Synechococcus* WH5701, SEQ ID NO: 10. |
| Soap Lake, WA | Alkaline, brackish | Cyanobacterium | *Nostoc* | n.d. |
| Soap Lake, WA | Alkaline, brackish | Bacteroidetes | Novel heterotroph | 97% identical to *Indibacter alkaliphile,s* SEQ ID NO: 11. |
| Soap Lake, WA | Alkaline, brackish | Cyanobacteria | *Merismopedia* | 99% identical to *Merismopedia glauca*, SEQ ID NO: 12. |

FIG. 1D

| Environment of Origin | Growth conditions | Type of Organism | Morphological Taxonomic Assignment | Molecular Taxonomic Assignment |
|---|---|---|---|---|
| Soap Lake, WA | Alkaline, brackish | Cyanobacteria | *Leptolyngbya* | 99% identical to *Leptolyngbya antarctica*, SEQ ID NO: 13. |
| Soap Lake, WA | Alkaline, brackish | Diatom | *Cymbella* | 100% identical to *Cymbella advena* chloroplast, SEQ ID NO: 14. | n.d. = not determined.

\* strains showed growth on pulp mill wastewater where chitin was added to the wastewater.

PROCESS OF TREATING BUCHU MERCAPTAN PRODUCTION WASTEWATER USING MICROALGAE AND CHITIN AS A NITROGEN SOURCE

CROSS-REFERENCE TO RELATED APPLICATIONS

This application is a continuation-in-part of U.S. application Ser. No. 14/181,387, filed on Feb. 14, 2014, now U.S. Pat. No. 9,102,552 B2, issued Aug. 11, 2015, which is a divisional of U.S. application Ser. No. 13/430,486, filed on Mar. 26, 2012, now U.S. Pat. No. 8,673,619, issued Mar. 18, 2014, and claims the benefit of U.S. Provisional Application No. 61/467,869, filed Mar. 25, 2011, the disclosures of which are hereby incorporated by reference in their entirety including all figures, tables and drawings.

STATEMENT REGARDING FEDERALLY SPONSORED RESEARCH OR DEVELOPMENT

Not applicable.

REFERENCE TO SEQUENCE LISTING, A TABLE, OR COMPUTER PROGRAM LISTING COMPACT DISC APPENDIX

The Sequence Listing for this application is labeled "Seq-List.txt" which was created on Mar. 26, 2012 and is 18 KB. The entire contents of the sequence listing is incorporated herein by references in its entirety.

BACKGROUND OF THE INVENTION

Chitin is one of the most abundant polymers on the planet, yet it is highly insoluble and only a few organisms can degrade it down to simple monomers. It is a long chain polymer of N-acetylglucosamine that is produced by crustaceans (crabs, lobster, shrimp), mollusks, cephalopods (squid, octopus), insects, fungi, and yeasts. At present most known chitin degraders are microorganisms that are aerobic heterotrophs. In other words, they require oxygen to metabolize chitin as a source of energy, carbon, and nitrogen. Other chitin degraders require that an independent source of organic compounds be added to the culture medium as an energy source. Thus current schemes to use the microbial degradation of chitin as a source for biomass or biofuel production, large scale culture conditions require abundant aeration and for the oxygen tensions to be carefully monitored and controlled. For some species of microorganism, an external source of carbon and energy must be provided (in the form, for example, of yeast extract). Both of these requirements add significantly to the cost and energy required to carry out large-scale degradation of chitin for the purposes of biomass production.

A need remains for an efficient method that uses the abundant polymer chitin as a nitrogen source to produce biomass, particularly cyanobacterial or algal biomass, on a commercial scale. In order to make the subject process as carbon neutral as possible, the method should replace the use of carbon-intensive materials, such as conventional nitrogen-based fertilizers, with carbon neutral alternatives.

BRIEF SUMMARY OF THE INVENTION

The invention is a process of growing a culture of cyanobacteria or algae using a composition comprising chitin, an insoluble naturally occurring organic polymer, as a source of nitrogen for photosynthetic growth. This invention takes a current waste product (chitin) and converts it into photosynthetic biomass that has a large number of commercial uses. Commercial uses of the biomass includes the production of biofuels, renewable chemicals, natural pigments, nutraceuticals, feed or feed supplements for aquaculture or animals, carbohydrate components for chemical feedstocks, or organic crop fertilizers, or the production of naturally occurring sunscreen, anti-cancer, or anti-inflammatory compounds. The subject process can also be used to remove pollutants, such as phosphorus and humic substances, from nitrogen-deficient natural waters or nitrogen-deficient wastewaters, such as that produced by pulp and paper industries. Because chitin is a renewable source of carbon and nitrogen (as compared to conventional sources of nitrogen fertilizers), the biomass and commercial products that result from this process are elevated onto a more carbon neutral playing field.

Wastewater from buchu mercaptan production is nitrogen-deficient. This production wastewater can be high in phosphorus and strongly acidic (due to presence of phosphoric acid). Even if most of the buchu mercaptan is removed for commercial production, the water still retains a strong sulfurous odor. A number of microalgal strains (all capable of rapid growth at acidic pH values) that grow on diluted buchu mercaptan production wastewater (as a phosphorus source) and chitin (as the nitrogen source) have been identified. In the processes, the strong sulfurous odor is rapidly neutralized and the algae consume the phosphorus as they grow and metabolize. Because the phosphoric acid is consumed as a source of nutrients, the pH of the water is neutralized (from strongly or moderately acidic to near neutral pH).

BRIEF DESCRIPTION OF THE SEVERAL VIEWS OF THE DRAWINGS

FIG. 1A-D is a table of phototrophic organisms useful in the method of the subject invention that are able to grow on chitin as a sole nitrogen source, the table includes the origin and growth characteristics of each.

DETAILED DESCRIPTION OF THE INVENTION

The invention is a process by which a cyanobacterium or alga, in pure culture or in the presence of helper heterotrophs or other phototrophs, is grown using a composition comprising chitin as a source of nitrogen. This invention allows for large-scale commercial growth of photosynthetic biomass using a carbon neutral, renewable source of nitrogen.

Cyanobacteria and algae use light as an energy source. Many cyanobacteria in the SYN-PRO clade, a related group that contains *Synechococcus, Prochlorococcus*, and *Cyanobium* species, as well as species in the Nostocales, have genes related to known chitinases in their genomes. These organisms, however, have not yet been demonstrated in the literature as being able to grow on chitin as a sole source of nitrogen.

Laboratory bench-scale (up to 3 liters) growth experiments show that many cyanobacterial taxa readily bind to purified chitin, and grow on chitin as a sole source of nitrogen. In addition, many different species of microalgae can grow in culture media using chitin as a sole source of nitrogen. The presence of helper heterotrophs (which by themselves may or may not be able to grow on chitin as a nitrogen or energy source) sometimes enhances the growth of the phototrophs in culture media containing chitin. The helper heterotrophs use carbon compounds and oxygen secreted by the phototrophs and therefore an external source of organic carbon or oxygen is not required for this heterotrophs to grow. Since many cyanobacterial cells are released from the chitin particles into the culture medium, the biomass that is released can be readily harvested and used for various industrial purposes. For filamentous cyanobacteria that burrow into the solid chitin particles, biomass or biomolecules can be readily harvested using various extraction techniques such as those that use supercritical fluids, organic solvents, or Soxhlet extraction.

Laboratory bench-scale experiments show that a variety of cyanobacterial taxa (unicellular and filamentous forms) as well as small unicellular and colonial algal taxa can be isolated on chitin as the sole source of nitrogen from enrichment cultures inoculated using a variety of environmental samples such as those deriving from freshwater, seawater, evaporites (crystals from evaporated seawater), soil, and alkaline saline lakes.

Commercial production-scale growth (2000 liters) has been accomplished using a selected cyanobacterium (*Cyanobium*) in a photobioreactor using crude, unpurified chitin derived from lobster shells.

The photosynthetic organisms useful in the method of the subject invention grow in an aqueous medium. The aqueous medium can be, for example, tap water, well water, distilled water, reverse osmosis water, filtered water, purified water, sea water, rain water, grey water, river water, lake water, pond water, groundwater, or wastewater. The water can be used unfiltered, unsterilized, or in an unpurified form. Alternatively, the water can be filtered, sterilized, or purified by running through ion exchange columns or charcoal filter, for example. Nutrients can be added to the aqueous medium, if they are not already present in sufficient quantities to support cyanobacterial or algal growth. Added nutrients can include, but are not limited to, iron, magnesium, calcium, sodium, potassium, phosphorus, sulfur, chloride, and trace metals. The salinity and the pH of the medium can be adjusted, if needed, to suit that of the photosynthetic organism being used. A composition comprising chitin is added to the aqueous medium as the source of nitrogen. This can be purified chitin, partially purified chitin, or raw unpurified chitin, that is ground coarsely or finely. An inoculum of cyanobacterial or algal culture is added to the medium. One or more photosynthetic organisms may be present in the inoculum. An example of one method to enrich or isolate photosynthetic organisms capable of growing on chitin is provided below (Example 1). The medium and cells are exposed to sun light, to artificial light, or a mixture of natural and artificial light, to allow the phototrophic cells to grow. This can be accomplished using any type of growth platform including culture flasks, bottles, and tubes, outdoor or indoor raceway ponds, plastic bags or tubes, or a commercial photobioreactor of any design. The cells are provided a source of carbon dioxide, such as air, enriched or pure carbon dioxide, flue or combustion gases, or fermentation gases. Some amount of time is allowed to pass, during which cyanobacterial or algal cells divide and produce biomass. During growth the medium may or may not be circulated using a water wheel, paddle, a pump, or by pumping air or gas through the medium. Finally, once the desired amount of growth has been achieved, the biomass is harvested.

Natural waters or wastewaters, if they have not been filtered or sterilized, can contain cyanobacteria or algae that are capable of growing using chitin as a source of nitrogen. Therefore if ground chitin is added to such natural waters or wastewaters, cyanobacterial or algal biomass can be grown in the absence of an added inoculum of photosynthetic organisms. Nutrients can be added to these natural waters, if they are not already present in sufficient quantities to support cyanobacterial or algal growth. The water and chitin mixture must then be incubated in artificial or natural light, a source of carbon dioxide applied, and then after time has been allowed to pass the biomass can be harvested (as described above).

The Cyanobacterium or alga may or may not be able to grow on chitin as a sole source of nitrogen in pure culture. Some species or strains may need the presence of an additional heterotroph or heterotrophs in order to produce photosynthetic biomass in culture media where chitin is the only supplied source of nitrogen. In this case, the heterotrophs help to break down the chitin polymer, partially or completely, secreting nitrogen containing compounds that are the result of the break down of chitin by the heterotrophs. The photosynthetic cyanobacterium or alga can then take up these break down products and use these as a source of nitrogen to support photosynthetic growth. These heterotrophs may be naturally present in the culture medium or the culture inoculum, may be naturally present in the water or wastewaters, or they may be added artificially to the culture medium when the photosynthetic organisms are inoculated into the culture medium. Species that have been demonstrated to grow using chitin as a source of nitrogen with or without helper heterotrophs are several related and unrelated species of cyanobacteria, green algae, eustigmatophytes, and diatoms (see FIG. 1). Other organisms that would be useful for the invention include red algae, stramenopiles other than eustigmatophytes, dinoflagellates, cryptomonads, euglenozoa, glaucophytes, and haptophytes.

Some cyanobacterial or algal strains may prefer to grow using chitosan (a polymer related to chitin where some or many N-acetylglucosamine residues have been deacetylated). Naturally-occurring chitin has some varying abundance of chitosan. Thus, some photosynthetic strains may be able to be grown using ground purified chitosan, partially purified chitosan, naturally occurring mixtures of chitin and chitosan, or unpurified chitosan. The chitosan can be produced naturally by an organism, enzymatically, or chemically by the artificial treatment of chitin.

Two important industrial uses are the production of cyanobacterial or algal biomass for a source of a slow-releasing organic fertilizer and the production of biomass for the purposes of biofuel or biodiesel production. Various subcomponents of the biomass can be extracted or concentrated for industrial applications such as the production of renewable chemicals, natural pigments (such as carotenoids, chlorophylls, accessory light harvesting pigments, natural UV sunscreens like scytonemin), nutraceuticals (such as omega-3 fatty acids and cholesterol-like compounds such as sitosterol), or carbohydrate components of the cell can be used for chemical feedstocks. Whole cell biomass or extracted subcomponents of the biomass can be used as feed or feed supplements for aquaculture (for example, the farming of fish or shellfish) or for animals (for example, for livestock). Organic compounds produced or secreted by cyanobacteria grown on chitin include the production of naturally occurring anti-cancer or anti-inflammatory compounds.

In another preferred embodiment, the process of the subject invention can be used to remove pollutants, such as phosphorus, from nitrogen-deficient natural waters or from nitrogen-deficient wastewaters, such as that produced by pulp and paper mill industries. Bench-scale experiments have shown that several chitin-utilizing phototrophic strains can grow on pulp wastewater that has undergone primary and secondary treatment where chitin has been added as the nitrogen source (see FIG. 1). Algal or cyanobacterial growth removes pollutants from the wastewater by trapping it into biomass (see, U.S. Pat. No. 8,101,080 B2). Such pollutants could include metals, phosphorus, humic substances, and PCBs (polychlorinated biphenyls). The biomass can be harvested, leaving clean, or cleaner, water behind. Finally, the biomass can be harvested for use in a large number of commercial purposes, as outlined above. A similar method can be employed to remove pollutants from contaminated natural waters. Lakes, ponds, rivers, or groundwaters that are nitrogen-deficient but contain pollutants such as phosphorus can be cleaned using a similar approach.

The advantage of using a cyanobacterium or alga to degrade chitin is that the culture does not need to be aerated (indeed cyanobacteria and algae produce their own oxygen). Also, an additional external carbon source does not need to be added to the process. Light, however (either natural or artificial), does have to be applied to the culture chamber.

This invention provides an improved method for producing large amounts of photosynthetic biomass for commercial purposes in a renewable, sustainable fashion. One of the biggest impediments to more wide spread use of algae in the production of feedstocks or biofuels has been the requirement for expensive and carbon-intensive conventional sources of nitrogen fertilizers such as urea, nitrate, or ammonia. Conventional fertilizers have enormous carbon footprints because large amounts of coal are needed for their synthesis from $CO_2$ gas via the Haber-Bosch process. Chitin is a waste product: most of the chitin derived from the harvesting of shellfish in the United States is currently trucked to the landfill. The amount of chitin available for implementation as a substrate for algal growth is therefore enormous: even a small seafood harvester on the East Coast of Maine processes 20,000 lb of lobster meat per day. Minimal processing of chitin from crab or lobster shells can make it a substrate for algal growth. Because the phototrophs use chitin as a source of nitrogen (and not energy), relatively small amounts of chitin can be readily converted into large amounts of algal biomass. Shellfish are sustainably harvested, and thus the chitin that derives from it is carbon neutral. Thus the invention outlined here now places large-scale commercial production of photosynthetic biomass on a higher, more sustainable playing field.

A preferred embodiment of a cyanobacterium and a heterotroph that can be used in the method of the subject invention includes, but is not limited to, a novel cyanobacterium (a close relative of *Cyanobium*, based on 16S ribosomal RNA sequencing) and a heterotroph (a member of the Bacteroidetes) isolated from Soap Lake, Wash. Each independently grow slowly on a simple mineral salts medium in the presence of chitin (see Example 2, below). However, when grown together in a co-culture both cells grow rapidly (doubling time of 10-11 hours) on chitin, resulting a pink culture (due to the presence of chlorophyll and carotenoids in the *Cyanobium* with abundant cells, $3 \times 10^7$ cells/mL). This strain can also grow on chemically prepared chitosan in the presence of heterotrophic bacteria. Related cyanobacteria that also grow on chitin have been isolated from the Bitterroot River, Mont., Holland Lake, Mont., and Red Alkali Lake, Wash.

Another preferred embodiment of a pure isolated cyanobacterium that can be used in the method of the subject invention includes, but is not limited to, a novel cyanobacterium (a close relative of *Nodularia harveyana*) isolated from commercial sea salt (Celtic Sea Salt, produced by the Grain and Salt Society in Brittany, France, obtained from a health food store). This filamentous strain grows best on chitin as a sole nitrogen source, grew well on nitrate, but somewhat poorly on nitrate, urea, N-acetylglucosamine, or in the absence of nitrogen. Related cyanobacteria that also grow on chitin have been isolated from Red Alkali Lake, Wash., and Soap Lake, Wash.

Another preferred embodiment of a pure isolated cyanobacterium that can be used in the method of the subject invention includes, but is not limited to, a novel cyanobacterium (a close relative of *Leptolyngbya antarctica*) isolated from Soap Lake, Wash. This filamentous strain grows best on chitin or urea as a sole nitrogen source. It also grew well on nitrate, but somewhat poorly on ammonia or N-acetylglucosamine. Related cyanobacteria that also grow on chitin have been isolated from commercial sea salt, iron rich desert soil from Sedona, Ariz., Soap Lake, Wash., and an open freshwater algae pond in Corvallis, Mont.

Another preferred embodiment of a pure isolated cyanobacterium that can be used in the method of the subject invention includes, but is not limited to, a novel cyanobacterium isolated from red oxidized desert soil from Sedona, Ariz. (this strain shows only distant similarity with other cyanobacterial taxa). This strain grows best on nitrate, urea, and chitin.

Another preferred embodiment of an alga that can be used in the method of the subject invention includes, but is not limited to, a novel green alga (a close relative of *Auxenochlorella prototheocoides*) isolated from the Bitterroot River, Mont. This alga grows best on chitin or nitrate as a sole source of nitrogen. It grows well on urea, and somewhat slowly on ammonia or N-acetylglucosamine. This particular strain grows well on pulp wastewater when chitin is added to the wastewater and incubated under the light. Other green algal strains related to *Auxenochlorella* and *Chlorella* that also grow on chitin have been isolated from commercial sea salt, Red Alkali Lake, Wash., and Soap Lake, Wash.

Another preferred embodiment of an alga that can be used in the method of the subject invention includes, but is not limited to, a novel motile green alga (related to *Dunaliella*) isolated from commercial sea salt. This alga was purified from an isolated green colony growing on a petri plate containing chitin, and grows well on nitrate or chitin as a sole source of nitrogen.

Another preferred embodiment of an alga that can be used in the method of the subject invention includes, but is not limited to, an alga in the Eustigamtophyceae (100% identical to *Nannochloropsis salina*) isolated from Puget Sound water. Unialgal cultures in the presence of heterotrophic bacteria grew well on chitin. However, antibiotic treated cultures of this particular strain that underwent serial dilution were later shown to grow poorly on chitin. The pure alga grows best on nitrate and ammonia, grows well on urea and slowly on N-acetylglucosamine.

Another preferred embodiment of an alga that can be used in the method of the subject invention includes, but is not limited to, a novel diatom (isolated from the Bitterroot River, closely related to *Cymbella* spp.). This strain grows best on nitrate, ammonia, and urea as nitrogen sources. It grows well on N-acetylglucosamine, but only slowly on chitin. Other related diatom strains have been isolated from iron rich desert soil from Sedona, Ariz. and Soap Lake, Wash.

Buchu mercaptan [5-methyl-2-(2-sulfanylpropan-2-yl)cyclohexan-1-one, buchu ketone, buchu replacer, thiomenthone, para-mentha-8-thiol-3-one, mercapto-8 paramenthanone-3, p-menthene-8-thiol-3-one, and various isomers] is a volatile organosulfur compound containing a ketone moiety attached to a hexane ring. It is used in the flavor and fragrance industries, and has typically been derived from extracts of the Buchu plant from South Africa (*Agathosma betulina*). Recently, chemical industries are beginning to develop synthetic methods for the production of this and related compounds (such as buchu mercaptan acetate). This synthetic process can result in the production of large volumes of acidic wastewater. This wastewater needs to be treated (pH neutralized, odor removed, in some regulatory regimes the phosphorus needs to be removed as well) before it can be discharged into the sewer or into the natural environment.

In another preferred embodiment, the process of the subject invention can be used to teat wastewater from buchu mercaptan production. A number of microalgal strains (all capable of rapid growth at acidic pH values) that are capable of growing on diluted buchu mercaptan wastewater (as a phosphorus source) and chitin (as the nitrogen source) have been identified. In the processes, the strong sulfurous odor is rapidly neutralized and the algae consume the phosphorus as they grow and metabolize. Because the phosphoric acid is consumed as a source of nutrients, the pH of the water is neutralized (from strongly or moderately acidic to near neutral pH). If chitin is put in sufficient excess in the culture, phosphorus could be largely removed from the wastewater thus eliminating any potential algal blooms that may result when this wastewater is discharged into the environment. Phosphorus is increasingly being regulated as a pollutant by the U.S. Environmental Protection Agency, so efficient and natural methods of reducing phosphorus pollution from wastewater sources are becoming increasingly desirable.

In a particularly preferred embodiment, microalgae growth is optimized in the subject process by diluting the buchu mercaptan wastewater. In the exemplified embodiments, the wastewater was diluted 0.1%. Dilutions can be made with material including, but not limited to, culture medium, other waste waters, or just water. One skilled in the art would understand that optimizing dilutions will vary with the strain of algae used as well as with the origin and type of wastewater and optimizing algael growth within the claimed process is well within the skill of the art.

The biomass produced through the process of wastewater treatment is a valuable commercial commodity. The biomass can be harvested and used directly as a feed supplement for aquaculture or for animal feed. Biomass components can be separated and sold individually. Such biomass components include oils (biofuels), proteins, natural food pigments, nutraceuticals (such as omega-3 fatty acids), and algae extracts for cosmetics and personal care products. The revenue generated from the sale of these bioproducts can help to offset the costs associated with the algal/chitin wastewater treatment system.

Growth of algae on wastewater (as the phosphorus source) and waste chitin (as the nitrogen source) means that algal biomass can be grown using low-cost sources of macronutrients. It also means that the greenhouse gas and energy footprints for the production of algal biomass can be greatly diminished. Conventional fertilizers (ammonium phosphate, ammonium nitrate, urea) have enormous greenhouse gas and energy footprints, because these compounds are synthesized using the Haber-Bosch process. Large amounts of fossil fuels are needed to carry out the Haber-Bosch process. The decreased greenhouse gas and energy footprints of the resulting biomass and biomass products make these bioproducts more desirable.

The following examples are offered to further illustrate but not limit both the compositions and the methods of the present invention. All percentages are by weight and all solvent mixture proportions are by volume unless otherwise noted.

Example 1—General Enrichment Culture and Strain Isolations

An example scheme for the enrichment of cyanobacterial or algal strains that grow on chitin is presented as follows.

Nitrogen-free culture medium that replicates or mimics the environmental conditions in which the water or surface sediment sample comes from is prepared and autoclaved. Example culture media includes BG-11 for the isolation of freshwater strains and ASN III for the isolation of marine strains. The media recipes are modified so that they omit any form of added nitrogen (nitrate or ammonia). Purified, ground, autoclaved chitin is added to the medium to the approximate final concentration of 0.5% in a sterile culture flask or bottle. One or several milliliters of freshly obtained water and/or surface sediment is added to the culture flask as the inoculum. This enrichment culture is incubated under the light (either natural sunlight or artificial light) until photosynthetic organisms appear (takes anywhere from 1-8 weeks). Cultures may or may not be shaken. Initially, heterotrophic bacteria and heterotrophic eukaryotes appear in the culture. However, it generally takes much longer incubation times before phototrophic cyanobacteria and algae begin to appear in the enrichment culture. Once phototrophic organisms become numerous, and either the chitin particles become colonized with pigmented cells or the aqueous medium becomes colored from abundant phototrophic growth, the phototrophs can be purified to obtain unialgal cultures using conventional microbiological techniques. These conventional techniques include serial dilution in medium that contains different sources of nitrogen (for example serial dilution on medium containing nitrate). Most resulting cultures are unialgal, in that they contain one phototrophic species but may contain one or several heterotrophic bacterial species. Pure cultures can be obtained by streaking petri plates that contain chitin or other sources of nitrogen. Antibiotic treatment alone or in combination with serial dilution can be used to reduce or eliminate the number of heterotrophic bacterial species in the culture. However, presence of the heterotrophic bacteria may aid photosynthetic growth on chitin, depending on the individual strain.

Example 2—Sampling, Enrichment Culture, and Isolation of *Cyanobium*

Five liters of surface water was collected from Soap Lake, Wash. on Mar. 28, 2010. The temperature of the water was 11.6° C., the pH was 9.83, and the conductivity was 23 mS. The water sample was transported back to the laboratory in Missoula, Mont. and was used to inoculate 25 mL culture media in 250 mL culture flasks that were incubated under a full-spectrum plant light at 18° C. The culture medium (Soap Lake autotrophic medium) contained (per liter): 1.5 g NaCl, 3.4 g $NaHCO_3$, 2.85 g $NaCO_3$, 0.95 g $Na_2HPO_4$, 2.5 g $Na_2SO_4$, 0.95 g KCl, 0.035 g $KNO_3$, 0.01 g $NH_4Cl$, 1.5 g $CaSO_4.2H_2O$, 2.45 g $MgCl_2.6H_2O$, 2.5 mL 1 mM EDTA, 2.5 mL ammonium-iron solution (1 mM $NH_4Cl$, 1 mM $Fe(III)Cl_3$, 2.5 mM sodium citrate, 0.025 N HCl) and 1 mL trace metal solution (per liter: 2.86 g boric acid, 1.81 g MnCl$_2$.4H$_2$O, 0.222 g ZnSO$_4$.7H$_2$O, 0.39 g NaMoO$_4$.2H$_2$O, 0.049 g CoCl$_2$.6H$_2$O), pH adjusted to 9.5. Measurement of cyanobacterial growth was monitored by red chlorophyll autofluorescence using a Nikon epifluorescence microscope at 400× magnification. A culture with a single cyanobacterium and a heterotroph was obtained by serial dilutions to extinction. A pure culture of the cyanobacterium was obtained by repeated serial dilution in culture medium that omitted sodium citrate. Elimination of the heterotroph was confirmed by Live:Dead (Molecular Probes, Invitrogen) fluorescence staining. A pure culture of the heterotroph was obtained from an isolated colony grown on Soap Lake autotrophic medium containing agar.

After 4 days' incubation, small, non-motile cocci that exhibited red chlorophyll autofluorescence were observed in the enrichment culture, consistent with the size and morphology of small-diameter *Synechococcus* and *Cyanobium* species. No cyanobacteria were observed in enrichment media where copper was present in the trace element solution. After multiple serial dilutions to isolate the cyanobacterium, it was observed that the culture contained two microorganisms—the cyanobacterium plus a non-photosynthetic heterotroph. To isolate the cyanobacterium in pure culture, multiple aggressive serial dilutions were performed in medium that lacked organic carbon. Elimination of the heterotroph was confirmed by staining the cells with the green stain from the Molecular Probes Live:Dead kit (which stained the heterotroph but not the cyanobacterium). Dense cyanobacterial cultures had a slight pinkish hue, and the accumulation of cells that sank to the bottom of the culture tube were a pinkish burgundy.

When plated on autotrophic medium containing agar, the heterotroph grew slowly, producing circular colonies that were 2-3 mm in diameter, had a somewhat irregular border, and were orange in color. Colonies grew equally well on plates incubated in the dark as the light. Cells occurred as cocci singly or in pairs as a result of binary fission, and were non-motile. The co-culture was reconstituted by mixing the pure cyanobacterium with heterotroph cells from an isolated colony. The resulting co-culture cell suspension was a moderate pink in color as a result of cyanobacterial growth.

In pure culture the exemplified *Cyanobium* grows well on nitrate and urea as a sole carbon source, and only weakly to poorly using ammonia. It grows poorly in the absence of added nitrogen, however this is likely due to trace impurities of nitrogen in either the culture reagents or the glassware (PCR results did not result in the amplification of a gene for nitrogenase). In pure culture, the exemplified Bacteroidetes heterotroph grows very poorly in the absence of spent culture medium from an old *Cyanobium* culture. Thus, the heterotroph likely uses organic compounds (unidentified) released by the *Cyanobium* into the culture medium as an energy source, as well as using the oxygen produced by the *Cyanobium* as a terminal electron acceptor.

The subject *Cyanobium* grows well under a wide variety of pH and salinity values. The optimal pH of growth was 9.0, however measured growth rates were significantly high between pH 7 and 10. The upper limit of growth was pH 10.5 (no growth at pH 10.5). The optimal salinity of growth was 0.6% NaCl, however growth rates were significant from 0.04% to 3% NaCl. Growth also occurred at 5% NaCl, however growth rates were lower.

Example 3—Enrichment and Isolation of *Nodularia* and *Nostocales* spp.

Commercial sea salt crystals were dissolved into N-free ASN III medium containing purified chitin and incubated at room temperature under artificial light. After several weeks, small intensely green clumps appeared on the chitin particles. Microscopic examination showed that these were colonies largely made of filamentous, heterocyst- or akinete-forming cyanobacterial filaments that belong to the *Nostocales* family. Enrichments of related cyanobacteria were also obtained from Red Alkali Lake, Wash., and from Soap Lake, Wash. Enrichment cultures, however, proved difficult to purify the *Nostocales* spp. from other phototrophs by serial dilution, even in culture medium lacking nitrogen (these strains are capable of fixing nitrogen and hence grow slowly in nitrogen-free media). Pure cultures were obtained by plating on solid medium containing nitrate or ammonia.

Example 4—Enrichment and Isolation of *Leptolyngbya* spp.

Commercial sea salt crystals were dissolved into N-free ASN III medium containing purified chitin and incubated at room temperature under artificial light. After several weeks, long, thin cyanobacterial filaments were observed microscopically using epifluorescence to be growing inside the chitin clumps. Eventually, this resulted in clumping of the chitin particles and the particles turning green.

For *Leptolyngbya* enrichments from Sedona soil or Soap Lake water, it was very difficult to obtain a unialgal culture by repeated serial dilution, even if the filaments were washed with nitrogen-free medium prior to serial dilution. Pure cultures were obtained by plating on solid medium containing nitrate or urea.

Example 5—Sampling, Enrichment Culture, and Isolation of Novel Cyanbacterium

Iron rich desert soil containing a microbial cryptobiotic crust in Sedona, Ariz. was sampled on Feb. 5, 2011. Material was transferred into Nitrogen-free BG-11 medium containing chitin as a nitrogen source and incubated under artificial light for several weeks. This resulted in an enrichment culture containing a diverse array of heterotrophs, cyanobacteria, and diatoms. Material was serially diluted on an array of different nitrogen sources (nitrate, ammonia, urea, and chitin). Each dilution was periodically examined and rediluted in order to isolate three cyanobacterial and one diatom strain. One cyanobacterial strain was observed to grow as paired rods. This strain grew well on nitrate, urea, and chitin as nitrogen sources. 16S ribosomal DNA sequencing showed that this strain is only distantly related to any known cyanobacteria (95% identical to *Acaryochloris*), and thus could comprise a novel genus or family.

Example 6—Sampling, Enrichment Culture, and Isolation of *Auxenochlorella* spp.

Surface water from the Bitterroot River was sampled from the boat launch at McClay Flat on Apr. 17, 2011, before the spring run off. The water temperature was 9.5° C. and the pH was 6.99. Water was inoculated into N-free BG-11 medium containing purified chitin and incubated for several weeks at room temperature under artificial light. Serial dilutions of the resulting enrichment culture on nitrate, ammonia, or urea led to the isolation of one cyanobacterium, a diatom, and a green microalga with morphology similar to *Chlorella*. 16S ribosomal DNA sequencing of the chloroplast genome showed that the green microalga was most closely related (98% identical) to *Auxenochlorella protothecoides*.

Additional *Chlorella* like strains have been isolated by enrichment on chitin followed by serial dilution from Red Alkali Lake, Wash., and Soap Lake, Wash. Similar strains have also been observed in enrichment cultures from various coastal marine waters collected around the United States.

Example 7—Enrichment Culture, and Isolation of *Dunaliella* spp.

Commercial sea salt crystals were dissolved into a modified *Haloarcula* medium (a hypersaline medium lacking organic carbon and nitrogen, with added phosphate, iron and trace elements) containing purified chitin and incubated at room temperature under artificial light. After several weeks, a pink enrichment culture resulted which contained abundant cells from the Halobacteriaceae as well as flagellated green microalgae with morphological features characteristic of *Dunaliella*. Streaking of the enrichment culture onto modified *Haloarcula* medium containing agar and chitin resulted in a small number of isolated dark green colonies and abundant pink colonies. The dark green colonies were comprised of *Dunaliella* cells and the pink colonies were comprised of archaea in the Halobacteriacaea. A single *Dunaliella* colony was transferred into liquid medium containing 1 mM nitrate. Growth was found to occur on marine medium (N-free ASN III with chitin), however growth in hypersaline medium resulted in higher cell densities.

Example 8—Sampling, Enrichment Culture, and Isolation of *Nannochloropsis* spp.

Seawater from the Puget Sound was collected in shallow water off on Nov. 27, 2010 from a public beach near Point Wilson Lighthouse, Port Townsend, Wash. This was inoculated into 25 mL N-Free ASN III medium containing 0.5% chitin, incubated at room temperature under artificial light. This strain did not grow well autotrophically in ASN III medium lacking chitin, but grew well in medium with chitin, nitrate, ammonium, or urea as the source of nitrogen. Antibiotic treatment (using kanamycin, chloramphenical, and spectinomycin) and serial dilution, coupled with growth on nitrate, was used to eliminate most of the bacteria in the original enrichment culture. The resulting antibiotic-treated strain grew well on nitrate, ammonia, or urea, but grew less well on chitin. Thus, heterotrophs likely enhance the growth rate of the organism on chitin. 16S ribosomal RNA analysis showed that this strain was 100% identical to *Nannochloropsis salina*.

Enrichment cultures of N-Free ASN III medium containing chitin, established from a wide variety of inocula from across the United States resulted in mixed cultures that contained *Nannochloropsis* and bacterial heterotrophs.

Example 9—Enrichment Culture and Isolation of *Cymbella* spp.

Enrichment cultures obtained from water from the Bitterroot River, Mont., contained diatoms (see also Example 6, above). The diatoms were purified by serial dilution in the presence of antibiotics. Sequencing of the chloroplast 16S ribosomal DNA gene shows that this alga is 97% identical to *Cymbella pisciculus*. Other diatom strains have been isolated from chitin grown enrichments from iron rich desert soil from Sedona, Ariz., and from alkaline Soap Lake, Wash. 16S ribosomal RNA shows that these three diatom strains are all very closely related, belonging to the genus *Cymbella*.

Example 10—Growth of Algal Strains on Diluted Buchu Production Wastewater with Chitin Buchu mercaptan production wastewater was diluted to 0.1% (pH 2.93, about 1 mM phosphate) using a modified synthetic culture medium (phosphorus-free, nitrogen-free BG-11 providing minimal cation and anions to support growth of freshwater microalgae). The pH of the mixture was adjusted to 4.2 and 4 cultures were set up. The first culture was a control with phosphorus-free BG-11 containing nitrate as the nitrogen source. The second culture contained 0.1% buchu mercaptan production wastewater in P-free N-free BG-11 where nitrate was the nitrogen source. The third culture contained 0.1% buchu wastewater in P-free N-free BG-11 where chitin was the nitrogen source. The cultures were inoculated with a mixture of three acidophilic algal cultures (a *Chlamydomonas*-like strain, a *Chlorella*-like strain, and an uncharacterized green microalgal strain). After several days' incubation, the first (control) culture showed growth of all three strains. The second culture showed little algal growth, and had a strong odor. The third culture showed moderate algal growth, and had no odor. After longer incubation, the pH of the tubes was measured. The positive control tube showed the pH had increased (from 4.2 to 6.8). Tube 2 showed only a small increase in pH (from 4.2 to 5.0). Tube 3 showed an increase in the pH (from 4.2 to 6.6).

Example 11—Growth of Additional Algal Strains on Diluted Buchu Production Wastewater with Chitin Buchu mercaptan production wastewater was diluted as in the previous example with P-free N-free BG-11 synthetic culture medium (pH adjusted to 4.2). The first culture contained nitrate as the nitrogen source and was inoculated with algal mix #1 (a *Chlamydomonas*-like strain, a *Chlorella*-like strain, and an uncharacterized green microalgal strain). The second culture contained nitrate as the nitrogen source and was inoculated with algal mix #2 (a green alga in the Coccomyxaceae, a second *Chlorella*-like strain, and an uncharacterized filamentous green alga). The third culture contained chitin as the nitrogen source and was inoculated with algal mix #1. The fourth culture contained chitin as the nitrogen source and was inoculated with algal mix #2. After several days' incubation, the tubes with nitrate as a nitrogen source showed little or no algal growth. However, the tubes with chitin as the nitrogen source were green and showed moderate algal growth. The tubes with nitrate as the nitrogen source had a strong odor, whereas the tubes with chitin as the nitrogen source had no odor. After additional incubation, the *Chlorella* and Coccomyxaceae strains showed the best growth, again with chitin as the nitrogen source. The tubes with nitrate as the nitrogen source showed a slight increase in pH (from 4.2 to 4.9 and 5.1). The tubes with chitin as the nitrogen source showed an increase in pH (from 4.2 to 6.4 and 6.5).

Example 12—Growth of Additional Algal Strains on Diluted Buchu Production Wastewater with Chitin Buchu mercaptan production wastewater was diluted to 0.1% with P-free N-free BG-11 synthetic medium where the pH was not adjusted (the pH of this water was 2.8). Two algal strains were tested (a *Chlorella*-like strain, and a strain in the Coccomyxaceae). Three nitrogen sources were tested (ammonia, nitrate, and chitin). After several days' incubation, there was little algal growth in the tubes with ammonia and nitrate. There was a strong odor of buchu mercapan in these tubes as well. The pH of these tubes ranged from 2.85 to 2.91. The tubes with chitin, on the other hand, showed moderate to good algal growth and had no buchu mercaptan odor. These tubes had pH values of 6.0 and 6.4.

It is understood that the foregoing examples are merely illustrative of the present invention. Certain modifications of the articles and/or methods employed may be made and still achieve the objectives of the invention. Such modifications are contemplated as within the scope of the claimed invention.

The invention claimed is:

1. A method of treating wastewater to remove at least one pollutant comprising the steps of:
    mixing a composition comprising at least one polymer selected from the group consisting of chitin and chitosan, and wastewater, wherein the wastewater is from the industrial production of a component selected from the group consisting of: buchu mercaptan and buchu mercaptan acetate;
    inoculating the mixture with at least one photosynthetic organism that uses chitin or chitosan, or a breakdown product of chitin or chitosan metabolism, as a nitrogen source;
    exposing the inoculated mixture to light;
    exposing the mixture to carbon dioxide;
    detecting growth of the at least one photosynthetic organism that uses chitin or chitosan, or a breakdown product of chitin or chitosan metabolism, as a nitrogen source;
    monitoring a level of pollutant in the inoculated mixture; and
    separating the solids of the inoculated mixture from the aqueous phase upon reaching a desired level of the at least one pollutant, wherein the aqueous phase has a reduced level of the pollutant.

2. The method of claim 1, wherein said method further comprises the step of inoculating the mixture with a heterotroph that supports the growth of said at least one photosynthetic organism that uses chitin or chitosan, or a breakdown product of chitin or chitosan metabolism, as a nitrogen source.

3. The method of claim 1, wherein said at least one pollutant is selected from the group consisting of phosphorous, acidity (acidic pH), mercaptans, and mercaptan odor.

4. The method of claim 1, wherein said wastewater is diluted.

* * * * *

SEQUENCE LISTING

```
<160> NUMBER OF SEQ ID NOS: 14

<210> SEQ ID NO 1
<211> LENGTH: 260
<212> TYPE: DNA
<213> ORGANISM: Leptolyngbya sp.
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t

<400> SEQUENCE: 1
aggaggcaag cgttatccag aattattggg cgtaaagcgt ccgcaggcgg ttaattaagt      60
ctgttgttaa agcccacagc tcaactgtgg atgggcaatg gaaactggtc aacttgagtg     120
cggtaggggt agagggaatt cccggtgtag cggtgaaatg cntatatatc gggaagaaca     180
ccagtggcga aggcnctcta ctgggccgna actgacgctg agggacgaaa gctaggggag     240
cgaaagggat tagataccccc                                                260

<210> SEQ ID NO 2
<211> LENGTH: 631
<212> TYPE: DNA
<213> ORGANISM: Nodularia sp.

<400> SEQUENCE: 2
gggtccgcag gtggccgtgt aagtctgctg ttaaagaatc tagctcaact agataaaagc      60
agtggaaact acacagctag agtgcgttcg gggtagaggg aattcctggt gtagcggtga     120
aatgcgtaga tatcaggaag aacaccagtg gcgaaggcgc tctactaggc cgcaactgac     180
actgagggac gaaagctagg ggagcgaatg ggattagata ccccagtagt cctagccgta     240
aacgatggat actaggcgtg gcttgtatcg acccgagccg tgccggagct aacgcgttaa     300
gtatcccgcc tggggagtac gcacgcaagt gtgaaactca aaggaattga cggggccccg     360
cacaagcggt ggagtatgtg gtttaattcg atgcaacgcg aagaaccttac ccaagacttg     420 acatgtcgcg aatcttcctg aaagggaaga gtgccttcgg gagcgcgaac acaggtggtg     480
catggctgtc gtcagctcgt gtcgtgagat gttgggttaa gtcccgcaac gagcgcaacc     540
ctcgttttta gttgccagca ttaagatggg cactctagag agactgccgg tgacaaaccg     600
gaggaaggtg gggatgacgt caagtcagca t                                    631

<210> SEQ ID NO 3
<211> LENGTH: 353
<212> TYPE: DNA
<213> ORGANISM: Nannochloropsis salina
<220> FEATURE:
<223> OTHER INFORMATION: chloroplast
```

<400> SEQUENCE: 3

```
acttactgag ttgtaaacct cggtacccta aggaagaaga tatgacggta cttagggtgg      60
aaagcatcgg ctaactccgt gccagcagcc gcggtaagac gggggatgca agtgttatcc     120
ggatttactg ggcgtaaagc gtctgcaggt ggtttcttaa gtctactgtt aaatcttgag     180
gctcaacctc aaatctgcag tagaaactag gagacttgag tatagtaggg gtagagggaa     240
tttccagtgg agcggtgaaa tgcgtagata ttggaaagaa caccgatggc gaaggcactc     300
tactgggcta ttactgacac tcagagacga aagctagggg agcaaatggg att           353
```

<210> SEQ ID NO 4
<211> LENGTH: 306
<212> TYPE: DNA
<213> ORGANISM: Auxenochlorella
<220> FEATURE:
<223> OTHER INFORMATION: chloroplast
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (190)..(190)
<223> OTHER INFORMATION: n is a, c, g, or t

<400> SEQUENCE: 4

```
aaactcttag gctagagttt ggtagggca gagggaattc ccggtggagc ggtgaaatgc       60
gtagagatcg ggaggaacac caaaggcgaa agcactctgc tgggccacan ctgacactga     120
gagacgaaag cgaggggagc aaaagggatt agataccct gtagtcctcg ccgtaaacga      180
tggatactan atgttgggga ggttaaatca ttcagtatcg tagctaacgc gtgaagtatc     240
ccgcctgggg agtatgctcg caagagtgaa actcaaggga attgacgggg gcccgcacaa     300
gcgggg                                                                306
```

<210> SEQ ID NO 5
<211> LENGTH: 756
<212> TYPE: DNA
<213> ORGANISM: Cymbella sp.
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (190)..(190)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t

<400> SEQUENCE: 5

```
tgacgtgtac ctgaagaata ancatcggct aactccgtgc cagcngccgc ggnaagacgg      60
aggatgcaag tgttatccgg aatcactggg cgtnaagcgt cngtaggtcg ttcaataagt     120
caactgttaa atcttgaggc tcaacttcaa aatcgcagtc gaaactatta aactagagta     180
tagtaggggn aaagggaatt tccagtggag cggtgaaatg cgtagagatt ggaaagaaca     240
ccaatggcga aagcacttta ctgggctatt actgacactg anagacgaaa gctagggtag     300
caaatgggat tagataccccc agtagtccta gccgtaaacg atggatacta gatgttgaac     360
agatcgacct gtgcagtatc aaagctaacg cgttaagtat cccgcctggg aagtatgctc     420
gcaagagtga aactcaaagg aattgacggg ggcccgcaca agcggtggag catgtggttt     480
aattcgatgc aacgcgaaga accttaccag ggtttgacat gatacgaatt tctttgaaag     540
aagaaagtgc cgtttggaac gtatacacag gtggtgcatg gctgtcgtca gctcgtgtcg     600
tgagatgttg ggttaagtcc cgcaacgagc gcaacccttà tttttagttg ccttatggaa     660
ctctaaaaag actgctggtt ataaaccgga ggaaggcggg gntgacgtca agtcagcatg     720
ccccttacac cctgggctac acacgtgcta caatgg                                756
```

<210> SEQ ID NO 6
<211> LENGTH: 796
<212> TYPE: DNA
<213> ORGANISM: Synechococcus
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (230)..(230)
<223> OTHER INFORMATION: n is a, c, g, or t
<220> FEATURE:
<221> NAME/KEY: misc_feature
<222> LOCATION: (614)..(614)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t

<400> SEQUENCE: 6

```
gcaatggaaa ctgctgggct agagtgtggt angggnagan ggaattcccg gtgtagcggt      60
gaaatgcgta gatatcggga agaacaccag tggcgaaggc gctctgctgg gccataactg     120
acgctcatgg acgaaagcca ggggagcgaa aggattaga taccccctgta gtcctggccg     180
taaacgatga acactaggtg tcgggggaat cgaccccctc ggtgtcntan ccaacgcgtt     240
aagtgttccg cctggggagt acgcacgcaa gtgtgaaact caaaggaatt gacggggcc     300
cgcacaagcg gtggagtatg tggtttaatt cgatgcaacg cgaagaacct taccagggtt     360
```

```
tgacatcctg cgaatccctt ggaaacttgg gagtgccttc gggagcgcag tgacaggtgg      420
tgcatggctg tcgtcagctc gtgtcgtgag atgttgggtt aagtcccgca acgagcgcaa      480
cccacgtctt tagttgccag catttagttg ggcactctag agagaccgcc ggtgataaac      540
cggaggaagg tgtggatgac gtcaagtcat catgcccctt acatcctggg ctacacacgt      600
actacaatgc tacngacaaa gggcagcaaa ctcgcgagag ctagcaaatc ccataanccg      660
tggctcagtt cagatcgtag gctgcaactc gcctacgtga aggaggaatc gctagtaatc      720
gcaggtcagc atactgcggt gaatacgttc ccgggccttg tacacaccgc ccgtcacacc      780
atggaagttg gccatg                                                     796
```

```
<210> SEQ ID NO 7
<211> LENGTH: 789
<212> TYPE: DNA
<213> ORGANISM: Cymbella sp.

<400> SEQUENCE: 7
gtggtcaaat aagtcaactg ttaaatcttg aggctcaacc tcaaaatcgc agtcgaaact      60
attagactag agtatagtag gggtaaaggg aatttccagt ggagcggtga aatgcgtaga     120
gattggaaag aacaccgatg cgaaggcac tttactgggc tattactaac actcagagac      180
gaaagctagg gtagcaaatg ggattagata ccccagtagt cctagctgta acaatggat      240 actagatgtt gaacatttga cctgtgcagt atcaaagcta acgcgttaag tatcccgcct     300
gggaagtatg ctcgcaagag tgaaactcaa aggaattgac ggggggccgc acaagcggtg     360
gagcatgtgt tttaattcga tgcaacgcga agaaccttac cagggtttga catgatacga     420 atttttcga aagaagaaag tgccgtttgg aacgtataca caggtggtgc atggctgtcg     480
tcagctcgtg tcgtgagatg ttgggttaag tcccgcaacg agcgcaaccc tcatttttag      540
ttgccttatg gaactctaga aagactgccg gttataaacc ggaggaaggc ggggatgacg     600
tcaagtcagc atgcccctta caccctgggc tacacacgtg ctacaatggg cgagacaatg      660
agatgcaact ctgcaaagac tagctaatct ataaactcgt tctaagttcg gattgtaggc     720
tgcaactcgc ctgcatgaag ttggaatcgc tagtaatcgc tggtcagcta cacagcggtg     780
aattcgttc                                                              789
```

```
<210> SEQ ID NO 8
<211> LENGTH: 779
<212> TYPE: DNA
<213> ORGANISM: Unknown
<220> FEATURE:
<223> OTHER INFORMATION: Cyanobacterium
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (658)..(658)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t

<400> SEQUENCE: 8
tgacggtacc tgaggaataa gcatcggcta actccgtgcc agcngccgcg gtaagacgga      60
```

-continued

```
ggatgcaagc gttatccgga attattgggc gtaaagcgtc cgcaggtggc tactcaagtc    120
tgttgtcaaa gcgcggggct taactccgta caggcaatgg aaactgagtg gctagagtat    180
ggtaggggta gagggaattc ccggtgtagc ggtgaaatgc gtagatatcg gaagaacac     240 cagtggcgaa agcgctctgc tggaccataa ctgacactga gggacgaaag ctangggagc    300
gaaagggatt agatacccct gtagtcctag ccgtaaacga tggacactag atgttgcccg    360
tatcgacccg ggcagtgtcg tagctaacgc gttaagtgtc ccgcctgggg agtacgctcg    420
caagagtgaa actcaaagga attgacgggg gcccgcacaa gcggtggagt atgtggttta    480
attcgatgca acgcgaagaa ccttaccagg gcttgacatg tcgcgaatcc ctctgaaagg    540
agggagtgcc ttcgggagcg cgaacacagg tggtgcatgg ctgtcgtcag ctcgtgtcgt    600
gagatgttgg gttaagtccc gcaacgagcg caaccctcgt ttttagttgc cagcattnag    660
ttgggcactc tagagagact gccggtgacn aaccggagga aggtggggat gacgtcaagt    720
cagcatgccc cttacgtcct gggctacaca cgtactacaa tgctacagac aaagggcag    779
```

```
<210> SEQ ID NO 9
<211> LENGTH: 609
<212> TYPE: DNA
<213> ORGANISM: Cyanobium
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
<222> LOCATION: (229)..(229)
<223> OTHER INFORMATION: n is a, c, g, or t
<220> FEATURE:
<221> NAME/KEY: misc_feature
<222> LOCATION: (232)..(234)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (246)..(247)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (255)..(256)
<223> OTHER INFORMATION: n is a, c, g, or t
<220> FEATURE:
<221> NAME/KEY: misc_feature
<222> LOCATION: (259)..(259)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
```

```
<221> NAME/KEY: misc_feature
<222> LOCATION: (270)..(271)
<223> OTHER INFORMATION: n is a, c, g, or t
<220> FEATURE:
<221> NAME/KEY: misc_feature
<222> LOCATION: (279)..(280)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (286)..(286)
<223> OTHER INFORMATION: n is a, c, g, or t
<220> FEATURE:
<221> NAME/KEY: misc_feature
<222> LOCATION: (288)..(289)
<223> OTHER INFORMATION: n is a, c, g, or t
<220> FEATURE:
<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (308)..(308)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t

<400> SEQUENCE: 9
tggaaactgg gaggctggag tggggtaggg gcagagggaa ttcccggtgt agcggtgaaa      60
tgcgtagata tcgggaagaa caccagtggc gaaggcgctc tgctgggcca taactgacgc     120
tcatggacga aagccagggg agcgaaaggg attagatacc cctgtagtcc tggccgtaaa     180
cgatgaacac taggggtcgg gggaatcgac ccccctcggtg tcgtanccna cnnnttaant    240
gtnccnnctg gngannacnc ncncaantgn naaaactcann ggantngnng ggggcccgca    300
caagnggngg antntgggtt taatttcgat gcaacgcgaa gaaccttacc agggtttgac    360
atcctgcgaa tctcttggaa acgagatatg gccttcggga gcgcagagac aggtggtgca    420
tggctgtcgt cagctcgtgt cgtgagatgt tgggttaagt cccgcaacga gcgcaaccca    480
cgtctttagt tgccagcatt tagttgggca ctctagagag accgccggtg ataaaccgga    540
ggaaggtgtg gatgacgtca agtcatcatg cccccttacat cctgggctac acacgtacta    600
caatgctac                                                            609

<210> SEQ ID NO 10
<211> LENGTH: 354
<212> TYPE: DNA
<213> ORGANISM: Cyanobium

<400> SEQUENCE: 10
ctctgggctg taaacctctt ttctcaagga agaagacatg acggtacttg aggaataagc      60
cacggctaat tccgtgccag cagccgcggt aatacgggag tggcaagcgt tatccggaat    120
tattgggcgt aaagcgtccg caggcggcct tttaagtctg ttgttaaagc gtggagctca    180
actccatttc ggcaatggaa actggaaggc tggagtgtgg tagggcagag ggaattccc     240 ggtgtagcgt tgaaatgcgt agatatcggg aagaacacca gtggcgaagg cgctctgctg    300
ggccataact gacgctcatg gacgaaagcc aggggagcga aagggattag atac           354
```

```
<210> SEQ ID NO 11
<211> LENGTH: 809
<212> TYPE: DNA
<213> ORGANISM: Unknown
<220> FEATURE:
<223> OTHER INFORMATION: Bacteroidetes
<220> FEATURE:
<221> NAME/KEY: misc_feature
<222> LOCATION: (44)..(44)
<223> OTHER INFORMATION: n is a, c, g, or t

<400> SEQUENCE: 11
gggtgcgtag gcggccttat aagtcagcgg tgaaatgcca gggntcaacc ccggcactgc      60
cgttgatact gttaggcttg agtgcgttct gggtacatgg aatttatggt gtagcggtga     120
aatgcataga taccataagg aacaccgata gcgaaggcat tgtactggga cgtaactgac     180
gctgatgcac gaaagcgtgg gtagcgaaca ggattagata ccctggtagt ccacgccgta     240
aacgatgatc actcgctgtc ctgcctatat ggtgtggcgg ccaagcgaaa gcgttaagtg     300
atccacctgg ggagtacgcc ggcaacggtg aaactcaaag gaattgacgg gggtccgcac     360
aagcggtgga gcatgtggtt taattcgatg atacgcgagg aaccttaccc gggctagaat     420
gtgaccgaag tatccagaga tggatgcgtc cgcaaggacg gaaaacaagg tgctgcatgg     480
ctgtcgtcag ctcgtgccgt gaggtgttgg gttaagtccc gcaacgagcg caaccccctat     540 tgtcagttgc catcaggtta agctggggac tctgacaaga ctgcctgcgc aagcagagag     600
gaaggagggg acgacgtcaa gtcatcatgg cccttacgcc cggggcgaca cacgtgctac     660
aatggcgcat acagcgggta gctacctggc aacaggatgc caacctctaa aagtgcgtct     720
cagttcggat cggggtctgc aacccgaccc cgtgaagctg gaatcgctag taatcgcgca     780
tcagccatgg cgcggtgaat acgttcccg                                         809

<210> SEQ ID NO 12
<211> LENGTH: 681
<212> TYPE: DNA
<213> ORGANISM: Merismopedia
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (313)..(313)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t
<220> FEATURE:
<221> NAME/KEY: misc_feature
<222> LOCATION: (346)..(346)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t

<400> SEQUENCE: 12
```

```
agcggtggaa actgcaagac tagagtacag taggggtagc aggaattccc agtgtagcgg      60
tgaaatgcgt agatattggg aagaacatcg gtggcgaaag cgtgctactg ggctgaaact     120
gacactgagg gacgaaagct agggtagcga aagggattag atacccctgt agtcctagcc     180
gtaaacgatg gatactaggc gtggcttgta tcgacccgag ccgtgccgaa nctaacgcgt     240
taagtatccc gcctggggag tacgcacgca agtgtgaaac tcaaaggaat tgacggggc      300 ccgcacaagc ggnggagtat gtggtttaat tcnatgcaac gcnaanaacc ttaccaaggn     360
ttgacatccc tggaatcttg cagaaatgcg agagtgcctt agggagccag gagacaggtg     420
gtgcatggct gtcgtcagct cgtgtcgtga gatgttgggt taagtcccgc aacgagcgca     480
accctcgttt ttagttgcca tcattaagtt gggcactcta gagagactgc cggtgacaaa     540
ccggaggaag gtggggatga cgtcaagtca tcatgcccct tacgccttgg gctacacacg     600
tactacaatg gtcgggacaa cgggcagcta accgcgagg tcaagcgaat cccatcnaac      660
ccggcctcag ttcagattgc a                                               681
```

<210> SEQ ID NO 13
<211> LENGTH: 789
<212> TYPE: DNA
<213> ORGANISM: Leptolyngbya
<220> FEATURE:
<221> NAME/KEY: misc_feature
<222> LOCATION: (41)..(46)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t

<400> SEQUENCE: 13

```
ccgtaggcgg cttttttaagt ctgttgtcaa agcccacagc nnnnnngtgg atcggcaatg     60
gaaactgggg agcttgagtg tggtaggggt agagggaatt cccggtgtag cggtgaaatg    120
cgtagatatc gggaagaaca ccagtggcga aggcgctcta ctgggccaca actgacgctg    180
atggacgaaa gctaggggag cgaaagggat tagataccc tgtagtccta gctgtaaacg     240
atggatacta ggtgttggac gtatcgaccc gtgcagtacc gtagctaacg cgttaagtat    300
cccgcctggg gagtacgcac gcaagtgtga aactcaaagg aattgacggg ggcccgcaca    360
agcggtggag gatgtggttt aattcgatgc aacgcgaaga accttaccaa ggcttgacat    420
gtcgcgaatc tttgcgagag cagagagtgc cttcgggagc gcgaacacag gtggtgcatg    480
gctgtcgtca gctcgtgtcg tgagatgttg ggttaagtcc cgcaacgagc gcaacccacg    540
tttttagttg ccagcattaa gttgggcact ctagagagac tgccgtggac aacacggagg    600
aaggtgtgga cgacgtcaag tcatcatgcc ccttacgtct gggctacac acgtcctaca     660 atgcttcgga cagagggcag caagccagcg atggttagca aatctcataa accgaggctc    720
agttcagatt gcaggctgca actcgcctgc atgaaggcgg aatcgctagt aatcgcangt    780
cagcatact                                                             789
```

<210> SEQ ID NO 14
<211> LENGTH: 819
<212> TYPE: DNA
<213> ORGANISM: Cymbella sp.

<400> SEQUENCE: 14

```
taggtggttt agtaagtcaa ctgttaaatc ttgaagctca acttcaaaat cgcagtcgaa     60
actattagac tagagtatag taggggtaaa gggaatttcc agtggagcgg tgaaatgcgt    120
```

```
agagattgga aagaacaccg atggcgaagg cactttactg ggctattact gacactcaga      180
gacgaaagct agggtagcaa atgggattag atacccagt  agtcctagcc gtaaacaatg      240
gatactagat gttgaacaga tcgacctgtg cagtattaaa gctaacgcgt taagtatccc      300
gcctgggaag tatgctcgca agagtgaaac tcaaaggaat tgacggggc  ccgcacaagc      360 ggtggagcat gtggtttaat tcgatgcaac gcgaagaacc ttaccagggt ttgacatgat      420
acgaatttct ttgaaagaag aaagtgccgt ttggaacgta tacacaggtg gtgcatggct      480
gtcgtcagct cgtgtcgtga gatgttgggt taagtcccgc aacgagcgca accctcattt      540
ttagttgcct ttatggaact ctagaaagac tgccggttat aaaccggagg aaggcgggga      600
tgacgtcaag tcagcatgcc ccttacaccc tgggctacac acgtgctaca atgggtgaga      660
caatgagatg caactctgcg aagacaagct aatctataaa ctcactctaa gttcggattg      720
taggctgcaa ctcgcctgca tgaagttgga atcgctagta atcgctggtc agctatacag      780
cggtgaatcc gttcccgggc cttgtacaca ccgcccgtc                             819
```